United States Patent [19]
Bajusz et al.

[11] Patent Number: 6,121,241
[45] Date of Patent: Sep. 19, 2000

[54] ANTICOAGULANT PEPTIDE ALDEHYDE DERIVATIVES

[75] Inventors: Sándor Bajusz; Attila Juhász; Éva Barabás; András Fehér; Gabriella Szabó ; Erzsébet Széll née Hasenöhrl; Irén Véghelyi née Fauszt; Emilia Lavich née Oszkó ; Éva Kaszás; József Langó ; Imre Moravcsik; Ágnes Szeker née Peszeky; Zsuzsanna Taschler née Pásztor; Gábor Tóth; Zsuzsanna Mohai née Nagy; Anna Mária Szalkay née Hollósi, all of Budapest; Klára Makk née Ocskay, Kismaros, all of Hungary

[73] Assignee: Gyogyszerkutato Intezet Kft., Budapest, Hungary

[21] Appl. No.: 09/011,001

[22] PCT Filed: Jun. 5, 1997

[86] PCT No.: PCT/HU97/00027

§ 371 Date: Apr. 2, 1999

§ 102(e) Date: Apr. 2, 1999

[87] PCT Pub. No.: WO97/46523

PCT Pub. Date: Dec. 11, 1997

[30] Foreign Application Priority Data

Jun. 5, 1996 [HU] Hungary ................................. 9601527

[51] Int. Cl.$^7$ ............................. A61K 38/05; C07K 5/00
[52] U.S. Cl. ................................ 514/19; 514/2; 514/822; 530/331; 548/535

[58] Field of Search .................................. 514/2, 19, 822; 530/331; 548/535

[56] References Cited

U.S. PATENT DOCUMENTS 4,703,036  10/1987  Bajusz et al. ............................. 514/18

FOREIGN PATENT DOCUMENTS 479489    4/1992   European Pat. Off. .
93/15756  8/1993   WIPO .
94/13693  6/1994   WIPO .

OTHER PUBLICATIONS

Bajusz et al., Bioorg. & Med. Chem. vol. 3, No. 8, pp. 1079–1089, 1995.
Bajusz et al., *J. Med. Chem.*, 33, 1990. 1729–35.
Shuman et al., *J. Med. Chem.*, 36, 1993, 314–319.

*Primary Examiner*—Bennett Celsa
*Attorney, Agent, or Firm*—Keil & Weinkauf

[57] ABSTRACT

This invention relates to peptide aldehyde derivatives of formula (I): D-Xaa-Pro-Arg-H, wherein Xaa represent a 2-cycloheptyl-2-hydroxyacetyl or 2-cyclopentyl-2-hydroxyacetyl group, Pro represents an L-prolyl residue and Arg represents an L-arginyl residue, their acid-additon salts formed with an organic or inorganic acid and pharmaceutical compositions containing the same. The compounds of formula (I) of the invention have therapeutic, particularly anticoagulant, antiplatelet and antithrombotic properties.

9 Claims, No Drawings

ANTICOAGULANT PEPTIDE ALDEHYDE DERIVATIVES

This is a 371 of PCT/HU 97/00027, filed on Jun. 5, 1997.

This invention relates to new peptide aldehyde derivatives of general formula (I), D-Xaa-Pro-Arg-H  (I)

wherein

Xaa represents a 2-cycloheptyl-2-hydroxyacetyl or 2-cyclopentyl-2-hydroxyacetyl group, Pro represents an L-prolyl residue and Arg represents an L-arginyl residue, their acid-addition salts formed with an organic or inorganic acid and pharmaceutical compositions containing the same.

The compounds of general formula (I) of the invention have valuable therapeutic, particularly anticoagulant, antiplatelet and antithrombotic, properties.

Particularly preferred representatives of the compounds of general formula (I) of the invention are the following derivatives:

D-2-cycloheptyl-2-hydroxyacetyl-L-prolyl-L-arginine aldehyde hemisulfate and

D-2-cyclopentyl-2-hydroxyacetyl-L-prolyl-L-arginine aldehyde hemisulfate.

Definitions

The abbreviations of the hydroxy- and aminoacids, their substituents and peptides built up therefrom are in accordance with the prior art, e.g. Biochem. J. 126, 773 (1972); Biochemistry 14, 449 (1975).

Amino Acids

Arg=L-arginine [(2R)-2-amino-5-guanidino-pentanoic acid],

Asp=L-aspartic acid [(2S)-2-amino-3-carboxypropionic acid], boroArg=L-boroarginine [(1R)-1-amino-4-guanidino-butylboric acid], D-Chg=D-2-cyclohexylglycine [(2R)-2-amino-cyclohexylacetic acid], D-cHga=D-2-cycloheptyl-2-hydroxyacetic acid [(2R)-2-cycloheptyl-2-hydroxyacetic acid], D-cPga=D-2-cyclopentyl-2-hydroxyacetic acid [(2R)-2-cyclopentyl-2-hydroxyacetic acid], Gla=gamma-carboxy-L-glutamic acid [(2S)-2-amino-4,4-dicarboxybutyric acid], Glu=L-glutamic acid [(2S)-2-amino-4-carboxybutyric acid], Gly=glycine (2-aminoacetic acid), D-Hma=hexahydro-D-amygdalic acid [(2R)-2-cyclohexyl-2-hydroxyacetic acid], D-MePhe=N-methyl-3-phenyl-D-alanine [(2R)-2-methylamino-3-phenylpropionic acid], D-MePhg=D-N-methylphenylglycine [(2R)-2-amino-2-phenylacetic acid], Nal(1)=3-(naphth-1-yl)-L-alanine [(2S)-2-amino-3-(naphth-1-yl)-propionic acid], D-Phe=3-phenyl-D-alanine [(2R)-2-amino-3-phenylpropionic acid], Pro=L-proline [(2s)-pyrrolidine-2-carboxylic acid].

Substituents

Ac=acetyl, Boc=tert-butoxycarbonyl,

Bz=benzoyl, Bzl=benzyl, Me=methyl, 4MeP=4-methylpentanoyl, pNA=p-nitrophenylamino, THP=tetrahydropyranyl, Tos=p-toluenesulfonyl, Z=benzyloxycarbonyl.

Peptides and Derivatives

The abbreviations of amino acids alone represent the respective L-amino acid. The D-amino acid is marked separately, e.g. 3-phenyl-D-alanine=D-Phe. The hyphen before and after the amino acid abbreviation means a missing hydrogen atom from the amino group or a missing hydroxy group from the carboxy group, resp. Accordingly, D-cHga-Pro-Arg-H represents D-cycloheptyl-2-hydroxyacetyl-L-prolyl-L-arginine aldehyde and Bz-Ile-Glu-Gly-Arg-pNA represents benzoyl-L-isoleucyl-L-glutamyl-glycyl-L-arginine p-nitroanilide.

DESCRIPTION OF THE RELATED ART

Blood clotting represents part of the protective mechanism in the organism. Vessel wall injury initiates the cascade, a blood clot is formed to inhibit bleeding to death. In addition, vascular diseases, haemostasis and pathological activation of clotting factors may also induce blood clotting. The vessel is obstructed fully or partially by the intravascular thrombus formed and thrombosis develops. Fibrinolysis represents an other part of the protective mechanism Here excess blood clots are removed by the enzymes participating in thrombolysis and the dissolution of the thrombus, too.

The blood clotting process is a cascade reaction, a series of catalyzed enzyme reactions, where plasma proteins, i.e. the clotting factors, are activated consecutively. The factors are designated by Roman figures, the active form is represented by the letter "a". Trivial names are in rise too, thus fibrinogen=factor I (fI), fibrin=factor Ia (fIa), prothrombin=factor II (fII) and thrombin=factor IIa (fIIa). Serine proteases (fXIIa, fVIIa, fXIa, fIXa, fXa and thrombin), some accelerating co-factors (fVa and fVIIIa) and the clottable molecule itself (fibrin) are all formed during the clotting process fXa and thrombin are the last two factors among the proteases formed. Thrombin, formed upon the action of fXa, initiates the fission of fibrinogen, resulting in the fibrin clot.

According to the earlier concept of blood clotting mechanism [R. G. MacFarlane, Nature 202, 498 (1964); E. W Davie and O. D. Ratnoff, Science 145, 1310 (1964)] fX is activated in two ways by an intrinsic and an extrinsic pathway. In the former case the process is initiated by the surface-activated fXII (fXIIa) with the transformation fXI→fXIa which is followed by the reaction fIX→fIXa; fX is activated by fIXa. In the extrinsic pathway the process is initiated by the appearance of the cellular surface receptor, the tissue factor (TF), and the development of the [fVIIxTF] or [fVIIaxTF] complex. fX is activated by the [fVIIaxTF] complex.

According to recent findings blood clotting in the living organism is a result of both pathways combined [E. W. Davie et al., Biochemistry 43, 10363 (1991)] where the main steps are the following:

1. In the case of vessel wall injury or disease TF migrates to the surface and binds a portion of factor VII circulating in the blood. The [fVII.TF]-complex formed is converted by the action of suitable trace amounts of proteases (e.g. fXIIa, fXa, fIXa and thrombin) into the active enzyme complex [fVIIa.TF] which activates a small portion of plasma factors IX and X (i.e. small amounts of fIXa and fXa are formed), then it is inactivated by the action of TFPI (Tissue Factor Pathway Inhibitor; earlier name LACI Lipoprotein-Associated Coagulation Inhibitor), the common inhibitor of both fXa and [fVIIaxTF]-complex [T. J. Girard et al., Nature 338, 518–520 (1989)].

2. The generated fIXa, together with factor X and cofactor VIIIa, produces, in the presence of $Ca^{++}$ ions, on a phospholipid surface (PL) the "tenase" complex, [fIXa.fVIIIa.fX.PL.Ca$^{++}$], wherein fX is activated to fXa.

3. The fXa generated up to this point, together with prothromnbin (fII) and cofactor fVa, produces the "prothrombinase complex" [fXa-fVa.fII.PL.Ca$^{++}$], which has a similar structure as "tenase". Here prothrombin is converted to thrombin. The fV→fVa and fVIII→fVIIIa conversions are performed either by fXa or thrombin.

4. The small amount of thrombin generated converts a portion of fXI to the enzyme fXIa and activates parts of factors VIII and V. to produce further amounts of fVIIIa and fVa, resp. By now fXIa can carry out the conversion of factor IX to the enzyme fIXa. With this step the chain reaction starting with the Xase-complex and terminated with thrombin formation is resumed. With the repetition of the process increasing amounts of thrombin are formed.

5. At a suitable high thrombin concentration the fibrinogen dissolved in the plasma undergoes partial proteolysis, a fibrin-monomer is generated which is first associated to the soluble fibrin polymer, then it is converted to insoluble fibrin polymer. Here also the thrombin is playing a role as fXIIIa, the factor performing polymerization, is produced upon its action [L. Lorand and K. Konishi, Arch. Biochem. Biophys. 105, 58 (1964)].

The insoluble fibrin polymer is the main component of the blood clot and thrombus, the other component is the blood platelet aggregate which is generated primarily upon the action of thrombin, too. The thrombus or blood clot formed entraps the major part of thrombin generated during the process which triggers a new coagulation process when it gets into the solution during the dissolution of the thrombus [A. K. Gash et al., Am. J. Cardiol. 57, 175 (1986); R. Kumar et al., Thromb. Haemost. 72, 713 (1994)].

The above features demonstrate the key role of thrombin in thrombus formation. Consequently, all compounds interfering with the function and/or formation of thrombin are of major importance in the therapy of thrombosis and related diseases.

At present the most widely and successfully used compounds applied for the prophylaxis and treatment of thrombosis are the heparins and the vitamin K antagonist coumarins (e.g. Syncumar and Warfarin) which are indirect thrombin inhibitors.

Heparin catalyses the reaction between thrombin and its natural inhibitor, antithrombin-III (AT-III). However, this action of heparin is absent if the plasma concentration of AT-III is tower than 75% of the normal level [R. Egbring et al., Thromb. Haemost. 42, 225 (1979)]. It is also of importance that the thrombin bound by the above-mentioned thrombus fails to be inhibited by this indirect mechanism as it is inaccessible to the heparin-AT-III-complex [J. I. Weitz et al., J. Clin. Invest. 86, 385 (1990)]. In addition, side effects such as treatment related haemorrhages and thromboembolies developing due to immunopathological processes are not negligible either [J. M. Walenga et al., Clin. Appl. Thrombosis/Hemostasis, 2(Suppl.1), S21–S27 (1996)].

The vitamin K antagonists may be administered also orally, their effect is developing after 16–24 hours. They inhibit the development of the reactive forms of some clotting factors with GIa content (i.e. prothrombin). To achieve therapeutic effects partial inhibition (60–70%) is required [M. P. Esnouf and C. V. Prowse, Biochim. Biophys. Acta 490, 471 (1977)] which may be attained by suitable drug dosage. The use of vitamin K antagonists, however, is not easy due to their narrow therapeutic range, strong dependence on diet composition (vitamin K) and variable individual sensitivity.

The first highly potent synthetic compound directly inhibiting thrombin was the tripeptide aldehyde D-Phe-Pro-Arg-H, a reversible inhibitor, exhibiting significant anticoagulant activity both in vitro and in vivo [S. Bajusz et al., in: Peptides Chemistry, Structure and Biology (R. Walter and J. Meienhofer, Eds.), Ann Arbor Publ., Ann Arbor, Mich., U.S.A., 603–608 (1975); Int. J. Peptide Protein Res. 12, 217 (1978)]. A series of compounds related to D-Phe-Pro-Arg-H have been synthesized. One of the first was Boc D-Phe-Pro-Arg-H [S. Bajusz et al., Int. J. Peptide Protein Res. 12, 217 (1978)] and the chloromethylketone analogue (D-Phe-Pro-Arg-CH$_2$Cl) which proved to be an irreversible inhibitor [C Kettner and E. Shaw, Thromb. Res. 14, 969 (1979)]. Further peptides and acylpeptides to be mentioned are the boroarginine analogues (D-Phe- and Boc-D-Phe- as well as Ac-D-Phe-Pro-boroArg) which are potent reversible thrombin inhibitors [C. Kettner et al., J. Biol. Chem. 265, 18289 (1990)] and other analogues of Boc-D Phe-Pro-Arg-H, including the Boc-D-Chg-Pro-Arg-H analogue [(P. D. Geseilchen and R. T. Shuman, European patent specification No 0,479,489 A2 (1992)].

In aqueous solutions D-Phe-Pro-Arg-H was prone to undergo spontaneous conversion, but D-MePhe-Pro-Arg H (CYKI-14766), obtained by methylating the terminal amino group, already proved to be of suitable stability while retaining the activity of the parent compound [S. Bajusz et al., U.S. Pat. No. 4,703,036 (1987); J. Med. Chem. 33, 1729 (1990)]. Blood clotting and thrombus formation were significantly inhibited in laboratory animals by the compound [D. Bagdy et al., Thromb. Haemost. 67, 357 and 68, 125 (1992), J. V. Jackson et al., J. Pharm Exp. Ther. 261, 546 (1992)]; its inhibitory action on the enzymes of fibrinolysis was negligible, co-administered with thrombolytics it significantly promoted the dissolution of the thrombus [C. V. Jackson et al., J. Cardiovascular Pharmacol. 21, 587 (1993)] which could not be attained with the heparin AT-III complex. Several compounds related to D-MePhe-Pro-Arg-H have been synthesized, e.g. D-MePhg-Pro-Arg-H [R. T. Shuman et al., J Med. Chem. 36, 314 (1993)].

New, stable and potent analogues of D-Phe-Pro-Arg-H have been obtained by substituting an α-hydroxyacyl group for the terminal Phe-moiety. Some of them, e.g. the D-2-cyclohexyl-2-hydroxyacetyl analogue, D-Hma-Pro-Arg-H, exhibited, similarly to C1, very high anticoagulant and antithrombotic effect [Hungarian patent specification No. 211,088; S. Bajusz et al, Bioorg Med. Chem. 8, 1079 (1995)].

Anticoagutant activity (i.e. inhibition of the proteolytic reactions in the process) is measured by anticoagulant tests, e.g. by the thrombin time (TT), activated partial thromboplastin time (APTT) and prothrombin time (PT) tests [E. J. W. Bovie et al; Mayo Clinic Laboratory Manual of Hemostasis; W. B. Sanuders Co., Philadelphia (1971)]. Plasma, inhibited in spontaneous coagulation, e.g. citrate-plasma, is made to coagulate and the required coagulation time is measured. Upon the action of anticoagulants the coagulation time is prolonged proportionally to the inhibition of the reaction(s) in the process. The anticoagulant effect can be characterized by the substance concentration required to double the coagulation time compared to the control (IC$_{50}$). The effect of anticoagulants on individual coagulant proteases is measured by the amidolytic method [R. Lottenberg et al., Methods in Enzymol. 80, 341 (1981); G. Cleason, Blood Coagulation and Fibrinolysis 5, 411 (1994)]. The isolated active factor (e.g. thrombin, fXa) and its chromogen or fluorogen peptide-amide substrate are reacted in the presence or absence of the inhibitor, resp. The enzyme inhibiting action is characterized by the inhibitory constant ($IC_{50}$) measured during amidolysis.

In the TT test coagulation is initiated by the thrombin added to the citrate plasma. In the system 22 pmol/mL of thrombin is functioning and in the presence of plasma components its inhibition can be measured on the fibrinogen (one of the natural substrates of thrombin) present In the APTT and PT tests the full coagulation process is made to proceed. Depending on the activator fX is activated by the extrinsic or intrinsic pathway. The generated fXa activates prothrombin to thrombin which, in turn, triggers plasma coagulation. In the test the coagulation time is prolonged if the enzymes or one of them is inhibited by the inhibitor. In the APTT and PT tests at most 40 pmole/ml Xa is generated (this is the full amount of factor X present in both systems) while 150 pmole/ml (APTT) and 350 pmole/ml (PT) are generated from thrombin [B Kaiser et al., Thromb. Res. 65, 157 (1992)].

In the case of D-MePhe-Pro-Arg-H (C1) the concentration doubling the clotting time in the TT, APTT and PT tests amounted to 87, 622 and 2915 nM, resp. These values and the amount of thrombin (22, 150 and 350 pmole/ml) functioning in the tests increased similarly, suggesting that C1 behaves as a thrombin inhibitor in both the APTT and the PT tests and had only slight or no influence on the function of fXa. In good agreement with these results the amidolytic effect of thrombin on the Tos-Gly-Pro-Arg-pNA substrate was inhibited by C1 with an $IC_{50}$=2 nM value, while the amidolytic effect of fXa on the corresponding Bz-Ile-Glu-Gly-Arg-pNA substrate was only slightly affected with an $IC_{50}$=9,1 mM value (Bajusz et at. unpublished results).

It is an inherent characteristic of the blood clotting mechanism that the process is inhibited not only by direct thrombin inhibitors but also by factors blocking thrombin formation, e.g. fXa inhibitors. The 60-member polypeptide isolated from tick, TAP (Tick Anticoagulant Peptide) [L. Waksman et al., Science 248, 593 (1990); A. B. Kelly et al., Circulation 86, 1411 (1992)] and DX-9065a (C2), a synthetic non-peptide, (+)-(2S)-2-[4[[(3S)-1-acetimidoyl-3-pyrrolidinyl]oxy]phenyl]-3-[7[amidino-2-naphthyl]-propionic acid hydrochloride pentahydrate [T. Hara et al., Throm. Haemost. 71, 314 (1994); T. Yokoyama et at., Circulation 92, 485 (1995)] are strong inhibitors of blood clotting and thrombus formation. Both the amidolytic effect and plasma clotting of fXa are strongly inhibited in the PT and APTT tests by these compounds, i.e. both the free and the complex-bound Xa factors are equally well inhibited while according to their nature as specific fXa inhibitors thrombin is not inhibited at all, i.e. they fail to exert any activity in the TT test. 4-MeP-Asp-Pro-Arg-H (C3) (international patent application No 93/15756) and Boc-D-Phe-Nal(1)-Arg-H (C4) (international patent application No. WO 94/13693) are synthetic peptide inhibitors of fXa. According to the literature C3 and C4 inhibit the amidolytic activity of fXa on the Z-D-Arg-Gly-Arg-pNA substrate at $IC_{50}$=57 and 30 nM, resp. No data are available on their anticoagulant potency. In our own tests C3 and C4 exhibited significant inhibition also on the Bz-Ile-Glu-Gly-Arg-pNA substrate while their anticoagulant activity proved to be negligible in the plasma clotting tests. The published (C2) and measured (C3–C4) activities of synthetic fXa inhibitors compared to the antithrombin compound C1 are presented in Table 1.

The data of Table 1 demonstrate that in the case of C1 the anticoagulant effect is due to the inhibition of thrombin while in the case of C2 it is due to the inhibition of fXa. The significant fXa inhibitory effect of C3 and C4 is not accompanied by any significant anticoagulant effect. Most probably the fXa active center in the prothrombinase complex is inaccessible to C3 and C4, these peptides can inhibit only free fXa in solution.

TABLE 1 fXa inhibiting (A) and anticoagulant (B) effect of known synthetic inhibitors

| Inhibitor | A: $IC_{50}$, $nM^b$ | B: $IC_{50}$, $\mu M^a$ | | |
|---|---|---|---|---|
| | | PT | APTT | TT |
| C1 | 9133 | 2.91 | 0.62 | 0.09 |
| C2 | 70 | 0.52 | 0.97 | $NA^c$ |
| C3 | 64 | 19.32 | 4.59 | 0.87 |
| C4 | 86 | 53.62 | 9.96 | 17.24 |

$^a$Peptide concentration doubling clotting time compared to the control in the prothrombin time (PT), activated partial thrombopastin time (APTT) and thrombin time (TT) test
$^b$Value measured with fXa on Bz-Ile-Glu-Gly-Arg-pNA chromogen substrate
$^c$NA = inactive According to a recent publication [N. A. Pager et al., Circulation 92, 962 (1995)] not only thrombin but also factor Xa, entrapped in the thrombus/blood clot and liberated during dissolution, contributes to the initiation and maintenance of a new coagulation process through the activation of the [fVII.TF] complex or factors V and VIII, resp. Consequently, it is advantageous if the anticoagulants are able to inhibit factor Xa in addition to the inhibition of thrombin, particularly if this inhibition is extended to thrombin and factor Xa entrapped in the clot.

BRIEF SUMMARY OF THE INVENTION

It is the objective of the present invention to prepare new peptide derivatives with improved anticoagulant activity compared to known compounds which exhibit anticoagulant activity also at oral administration.

It was observed that the amidolytic effect of factor Xa as inhibited at about 30 times lower $IC_{50}$ values by the known α-D-hydroxyacyl-L-prolyl-L-arginine aldehydes [S. Bajusz et al., Bioorg. Med. Chem. 8, 1079 (1995)] compared to C1 while they possessed similar significant anticoagulant activity. D-Hma-Pro-Arg-H (C5) is such a D-2-cyclohexyl-2-hydroxyacetyl analogue. It was unexpectedly found that the analogues obtained with 2-cycloheptyl-2-hydroxyacetic acid and 2-cyclopentyl-2-hydroxyacetic acid, D-cHga- and D-cPga-Pro-Arg-H, inhibit factor Xa even stronger while retaining significant anticoagulant effect, too.

DETAILED DESCRIPTION OF THE INVENTION

This invention relates to new peptide aldehyde derivatives of general formula (I),

D-Xaa-Pro-Arg-H    (I)

wherein

Xaa represents a 2-cycloheptyl-2-hydroxyacetyl or 2-cyclopentyl-2-hydroxyacetyl group, Pro represents an L-prolyl residue and Arg represents an L-arginyl residue, their acid-addition salts formed with an organic or inorganic acid and pharmaceutical compositions containing the same.

The compounds of general formula (I), wherein Xaa, Pro and Arg have the same meaning as above, are prepared by condensing an acyldipeptide Q-D-Xaa-Pro, protected on the hydroxy group with a Q protecting group, with an L-arginine lactam, protected on the guanidino group with a benzyloxycarbonyl group, and reducing the obtained protected peptide lactam to the protected peptide aldehyde of the formula Q-D-Xaa-Pro-Arg(Z)-H, finally removing the Z group from the guanidino group of arginine and the Q group from the α-hydroxy group, and isolating the peptide derivative of general formula (I) as its addition salt formed with an organic or inorganic acid.

The acyldipeptide Q-D-Xaa-Pro, used as starting material, is prepared by converting a D-Xaa α-hydroxyacid to a benzyl ester, protecting the hydroxy group with a Q group, converting the resulting Q-D-Xaa-OBzl by hydrogenolysis to the free acid, and coupling it to L-proline benzyl ester. The required O-protected acyl-dipeptide is obtained by removing the benzyl ester with hydrogenolysis.

Q-D-Xaa, the α-hydroxyacid protected by a Q group on the OH group and required for the coupling with proline, is advantageously prepared by O-acetylating the racemic DL-Xaa compound, then removing the acetyl group from Ac-D-Xaa by enzymatic hydrolysis. In a preferred process the racemic DL-Xaa can be resolved with D-tyrosine hydrazide, too.

Compounds of general formula (I) of the invention wherein Xaa, Pro and Arg have the same meaning as above, exhibit strong anticoagulant activity both in vitro and in vivo and possess excellent bioavailability.

The in vitro anticoagulant effect of the compounds of general formula (I) was measured by the prothrombin time (PT), activated partial thromboplastin time (APTT) and thrombin time (TT) tests [D. Bagdy et at., Thromb. Haemost. 67, 325 (1992)]. The Xa-factor-inhibiting effect of the compounds was also determined by using the Bz-Ile-Glu-Gly-Arg-pNA chromogen substrate (see method M6).

The results obtained are presented in Table 2. The corresponding data of C1 and C5 served as controls. In the Table the compounds are listed in the decreasing order of PT activity. The data definitely demonstrate the beneficial effect of the terminal cHga- and cPga-moieties compared to the Hma and MePhe residues.

TABLE 2

Anticoagulant (A) and factor Xa inhibiting (B) effect of the new peptidyl aldehydes of the invention and of control compounds having similar structure in the decreasing order of PT activity

| Peptidyl-arginine aldehyde (No.[b]) | A: $IC_{50}$, $\mu M^a$ | | | B: $IC_{50}$ nM[d] |
|---|---|---|---|---|
| | PT | APTT | TT | |
| D-cHga-Pro-Arg-H (1) | 1.20 | 0.37 | 0.11 | 63 |
| D-cPga-Pro-Arg-H (2) | 2.03 | 0.71 | 0.10 | 107 |
| Control compounds | | | | |
| D-Hma-Pro-Arg-H (C5) | 2.14 | 0.79 | 0.22 | 247 |
| D-MePhe-Pro-Arg-H (C1) | 2.92 | 0.62 | 0.09 | 9133 |

[a]Peptide concentration doubling thrombin time compared to control
[b]Identical to example number describing preparation of the respective compound and control (C1, C5)
[d]Value measured on substrate Bz-Ile-Glu-Gly-Arg-pNA with insulated human factor Xa (see methods M1–M5).

Table 3 demonstrates on compound No. 1 as an example the inhibitory effect of the compounds of general formula (I) on factor Xa, entrapped in plasma clot, and thrombin as well as on thrombin bound to fibrin gel; the corresponding data of C1 and C2 served as controls. The plasma clot was obtained by the recalcification of platelet-rich human citrate plasma and fibrin gel by the coagulation of human fibrinogen with human thrombin Z-D-Arg-Gly-Arg-pNA and Tos Gly-Pro-Arg-pNA were used as substrates for measuring the activity of factor Xa and thrombin (methods M1–M5).

TABLE 3

Inhibitory effect of the new peptidyl-arginine aldehyd (1) of the invention and control compounds (C1, C5) ($IC_{50}$, $\mu M$) on plasma clot entrapped factor Xa and thrombin as well as on fibrin-gel bound thrombin[a]

| Peptidyl-arginine aldehyde (No.[b]) | Plasma-clot | | Fibrin-gel |
|---|---|---|---|
| | Factor Xa | Thrombin | Thrombin |
| D-cHga-Pro-Arg-H (1) | 0.20 | 0.52 | 0.21 |
| Control compounds | | | |
| D-MePhe-Pro-Arg-H (C1) | 1.12 | 0.38 | 0.30 |
| D-Hma-Pro-Arg-H (C5) | 0.19 | 0.27 | 0.22 |

[a]Moc-D-Chg-Gly-Arg-pNA and Tos-Gly-Pro-Arg-pNA served as substrates for measuring the activity of factor Xa and thrombin at the determination of $IC_{50}$ values according to methods M1–M5
[b]Identical to example number describing preparation of the new compound and controls (C1, C5)

The data demonstrate that factor Xa and thrombin, entrapped in platelet-rich human plasma clot as well as thrombin bound to fibrin-gel are inhibited by compound (1) of the invention at $IC_{50}$ values lower than micromole/nanomol, similarly to compound C5.

The inhibitory effect of the new compounds of the invention on plasmin (PL) as well as on plasmin formation induced by tissue plasminagen activator (tPA) and urokinase (UK) was studied by the fibrin-platelet method [D. Bagdy et al.; Thromb. Haemost. 67, 325 (1992)]. Compounds C1 and C3 served as controls. The moderate antifibrinolytic action of C1 proved to be negligible in vivo and it could be used as an adjuvant at the dissolution of experimental thrombus while the antifibrinolytic activity of C3 was detectable in vivo [C. V. Jackson et al., J. Cardiovasc. Pharmacol. 21, 587 (1993)].

In Table 4 the results obtained with the new compounds 1 and 2 as well as with controls C1 and C3 are presented as an example. In addition to the $IC_{50}$ values (columns A) the efficacy of the compounds related to C1 are also listed (columns B). The latter data indicate that similarly to compound C1 the antifibrinolytic activity of the new compounds 1 and 2 is moderate, their activity against the 3 enzymes tested is 7.5–12–39 times lower than that of compound C3.

TABLE 4

The inhibitory effect ($IC_{50}$) of the new peptidyl-arginine aldehydes of the invention and of controls with similar structure on plasmin (PL) as well as on plasmin formation induced by tissue plasminogen activator (tPA) and urokinase (UK) studied by the fibrin-plate method[a]

| Peptidy-argininge aldehyde (No.[c]) | A: $IC_{50}$ and B: relative efficacy[b] | | | | | |
|---|---|---|---|---|---|---|
| | PL | | tPA | | UK | |
| | A | B | A | B | A | B |
| D-cHga-Pro-Arg-H (1) | 83 | 0.6 | 74 | 1.8 | 120 | 0.7 |
| D-cPga-Pro-Arg-H (2) | 3.9 | 0.13 | 112 | 1.2 | 137 | 0.6 |

TABLE 4-continued

The inhibitory effect ($IC_{50}$) of the new peptidyl-arginine aldehydes of the invention and of controls with similar structure on plasmin (PL) as well as on plasmin formation induced by tissue plasminogen activator (tPA) and urokinase (UK) studied by the fibrin-plate method[a]

| Peptidyl-argininge aldehyde | A: $IC_{50}$ and B: relative efficacy[b] | | | | | |
|---|---|---|---|---|---|---|
| | PL | | tPA | | UK | |
| (No.[c]) | A | B | A | B | A | B |
| D-MePhe-Pro-Arg-H (C1) | 54 | 1.0 | 132 | 1.0 | 82 | 1.0 |
| Boc-D-Phe-Pro-Arg-H (C3) | 12 | 4.5 | 6 | 22.0 | 3 | 27.3 |

[a]$IC_{50}$ = peptide concentration (mM) where the hydrolyzed area on the fibrin plate is reduced by 50% compared to the control
[b]Values related to the activity of C1 ($1/IC_{50}$ = 1)
[c]Identical to example number describing preparation of the respective compound and control (C1, C3)

The anticoagulant and platelet aggregation inhibiting effect of the compounds of general formula (I) was studied In New Zealand white rabbits ex vivo according to D. Bagdy et al [Thromb. Haemost 67. 357 (1992). The compounds were dissolved in buffered isotonic saline solution and administered i.v. (0,04–5.0 mg/kg) or by infusion (0.25–5.0 mg/kg/h) or subcutaneously (0.5–6.0 mg/kg) or p.o. (2.5–20 mg/kg). The effect of the compounds was detectable already within 30 minutes following p.o. administration, peak values were attained after 60–180 minutes and the therapeutic level was maintained dose-dependently for 3→6 hours.

The in vivo effect of D-cHga Pro-Arg-H (1) is presented in detail in Tables 5 and 6. The corresponding values of C1 are listed as controls. The compound was administered p.o. in doses of 5 mg/kg. The blood samples drawn from the caudal vein in every 30–60 minutes were analyzed. The whole blood clotting time (WBCT) and the inhibition of thrombin-induced blood platelet aggregation (PAI) were determined. The activated partial thromboplastin time (APTT) and the thrombin time (TT) in the citrate plasma obtained from the blood sample were also measured. The APTT and TT values are compiled in Table 5 and the WBCT and PAI values in Table 6.

TABLE 5

Anticoagulant effect of D-cHga-Pro-Arg-H and D-MePhe-Pro-Arg-H in rabbits at p.o. doses of 5 mg/kg in the APTT and TT tests characterized by relative clotting times[a]

| Time | D-cHga-Pro-Arg-H (1) | | D-MePhe-Pro-Arg-H (C1) | |
|---|---|---|---|---|
| min. | APTT | TT | APTT | TT |
| 0 | 1.0 | 1.0 | 1.0 | 1.0 |
| 30 | *2.01 ± 0.43* | *10.57 ± 5.98* | 1.27 ± 0.38 | 1.52 ± 0.17 |
| 45 | *2.25 ± 0.43* | *10.89 ± 5.89* | 1.30 ± 0.02 | 2.50 ± 0.44 |
| 60 | *2.32 ± 0.43* | *11.67 ± 5.69* | 1.37 ± 0.03 | *4.75 ± 1.38* |
| 90 | *2.11 ± 0.31* | *14.00 ± 6.48* | 1.45 ± 0.09 | *10.50 ± 5.49* |
| 120 | *1.84 ± 0.11* | *10.60 ± 4.22* | 1.43 ± 0.11 | *5.51 ± 3.59* |
| 180 | *1.66 ± 0.10* | 2.22 ± 0.71 | 1.39 ± 0.09 | 2.05 ± 0.38 |
| 240 | 1.37 ± 0.08 | 1.23 ± 0.07 | 1.31 ± 0.11 | 1.81 ± 0.39 |
| 300 | 1.31 ± 0.09 | 1.13 ± 0.05 | 1.25 ± 0.22 | — |

[a]Ratio of clotting times measured in treated and untreated animals. Therapeutic values are in italics.

татAB LE 6

Anticoagulant and blood platelet aggregation inhibiting (PAI) effect of D-cHga-Pro-Arg-H and D-MePhe-Pro-Arg-H in rabbits at p.o. doses of 5 mg/kg in the WBCT test characterized by relative clotting time and percentual inhibition[a]

| Time | D-cHga-Pro-Arg-H (1) | | D-MePhe-Pro-Arg-H (C1) | |
|---|---|---|---|---|
| min. | WBCT | PAI(%) | WBCT | PAI(%) |
| 0 | 1.0 | 0 | 1.0 | 0 |
| 30 | *1.80 ± 0.36* | *71.0 ± 19.4* | 1.07 ± 0.13 | *52.8 ± 14.7* |
| 45 | *2.03 ± 0.35* | *74.0 ± 13.9* | 1.26 ± 0.07 | *58.4 ± 15.6* |
| 60 | *1.98 ± 0.30* | *91.0 ± 4.5* | *1.55 ± 0.17* | *54.2 ± 11.6* |
| 90 | *1.78 ± 0.26* | *93.0 ± 3.5* | *1.61 ± 0.34* | *83.2 ± 8.9* |
| 120 | *1.52 ± 0.13* | *92.4 ± 6.5* | 1.45 ± 0.21 | *75.2 ± 12.3* |
| 180 | 1.29 ± 0.07 | *71.6 ± 19.8* | 1.44 ± 0.08 | 47.5 ± 20.9 |
| 240 | 1.13 ± 0.04 | 49.4 ± 21.5 | 1.22 ± 0.08 | 32.2 ± 16.0 |

[a]Ratio of clotting times measured in treated and untreated animals. Therapeutic values are in italics.

The data in the Tables show that the new compound 1 higher and more stable anticoagulant and blood platelet aggregation inhibiting activity than the control compound C1.

The compounds of the invention of general formula (I) are used for the treatment and prevention of the following diseases where thrombosis and/or hypercoagulability is involved deep venous thrombosis, pulmonary embolism, arterial thrombosis, unstable angina, myocardiac infarct, auricular fibrillation and thrombosis-based stroke. In atherosclerosis they may be used to prevent diseases of coronary arteries, thrombotic diseases of cerebral arteries, as a surgical prophylaxis of high risk patients or other surgical prophylaxis. They may be applied in the thrombolysis of percutaneous transluminal angioplastics for the prevention of reocclusion, for adjuvant therapy in nephrosis in the case of hemodialysis and in diseases with hypercoagulability: in malignant tumours and inflammation (e.g. arthritis) as well as in diabetes. They may be applied in cases where the administration of other anticoagulants fails to be effective or is contraindicated, e.g. lack of antithromrbin-III in the case of heparin or heparin-induced thrombocytopenia (HIT), and in the case of coumarins, e.g. pregnancy.

The compounds of the invention and their pharmaceutically acceptable salts are used for therapeutic purposes alone or preferably in the form of a pharmaceutical formulation. The invention also refers to these formulations.

The pharmaceutical formulations comprise an effective amount of a compound of general formula (I) or a pharmaceutically acceptable salt thereof and known pharmaceutically acceptable carriers, filling materials, diluents and/or other pharmaceutical excipients The above carriers, diluents or filling materials can be water, alcohols, gelatin, lactose, saccharose, starch, pectin, magnesium stearate, stearic acid, talcum, various oils of animal or plant origin, furthermore glycols, e.g. propylene glycol or polyethylene glycol. The pharmareutical excipients can be preservatives, various natural or synthetic emulgeators, dispersing or wetting agents, colouring materials, flavouring agents, buffers, materials promoting disintegration and other materials improving the bioavailability of the active ingredient.

The pharmaceutical compositions of the invention can be prepared in usual formulations such as oral compositions (administered through the mouth such as tablets, capsules, powders, pills, dragees or granulates) as well as parenteral compositions (drugs administered by avoiding the gastrointestinal system such as injections, infusions, suppositories, plasters or ointments).

The therapeutic dose level of the compounds of the invention depends on the individual health status and age of the patient and may vary accordingly, consequently, its level is fixed by the physician designing treatment In diseases where inhibiton of the function and/or formation of thrombin is required for prophylactic or therapeutic purposes a daily oral or parenteral (e.g. i.v.) dose of 0.01 to 1000 mg/kg body weight, preferably 0.25 to 20 mg/kg body weight, may be administered.

The compounds of general formula (I) of the invention, administered together with thrombolytic agents (e.g. tPA or urokinase), actively promote the dissolution of thrombi formed in arteries or veins and efficiently prevent their reformation In such cases it is preferred to administer the compounds of the invention simultaneously with thrombolytic agents or immediately after thrombolytic treatment.

The following examples are illustrating but not limiting the scope of the invention.

The R, values recorded in the examples were determined by thin-layer chromatography, using silica gel as adsorbent (DC-Alufolien Kieselgel 60 $F_{254}$, Merck, Darmstadt), in the following developing solvents:

1. Ethyl acetate
2. Ethyl acetate—pyridine—acetic acid—water (480:20:6.11)
3. Ethyl acetate—pyridine—acetic acid—water (60:20:6:11)
6. Ethyl acetate—pyridine—acetic acid—water (240:20:6:11)
12. Ethyl acetate—cyclohexane (1:9)
14. Chloroform—acetic acid (95:5)

The capacity factors (k') specified in the examples were determined with the apparatus "Pharmacia LKB Analytical HPLC System Two" as follows:

Column: "VYDAC C-18 reversed phase: 10 $\mu$m, 300 A, 50 mm"

Buffer A: 0 1% trifluoroacetic acid in water

Buffer B 0.1% trifluoroacetic acid in acetonitrile

Gradients applied (flow rate) at 1 ml./min.

I: 0–5 min. 0–25% B, then isocratic 25% B;

II: 0–30 min 0–60% B.

The gradient applied in the HPLC analysis (I or II) is specified in brackets after the abbreviation at the individual steps of the examples.

Optical purity was determined with the above HPLC apparatus as follows and indicated with the expression "chiral HPLC" in brackets:

Column: Chiralpack WH (DAICEL) 4×250 mm

Eluant: 0.25 mM $CuSO_4$; flow rate 1 ml./min.

Analyses were performed at 50° C.

The peptide content of the eluate was detected in UV light at 214 nm. Sample concentration: 1 mg/mL in buffer A (reverse phase) or methanol (chiral phase) resp., injected volume 25 $\mu$L.

The acylarginine aldehydes are present in equilibrium structures, i.e. in aldehyde, aldehyde hydrate and two aminocyclol forms. During HPLC analysis the aldehyde hydrate and one or both aminocyclol forms appear as separate peaks, consequently the acylarginine aldehydes described in the examples are specified by two or three k' values.

Mass spectrometry. The FAB positive ionization measurements were performed in a Finnigan MAT 8430 apparatus. The samples w,ere dissolved in m-nitrobenzylalcohol matrix and introduced directly into the ion source. In the spectrum of peptidyl-arginine aldehydes an additional molecule ion was detectable, that of the addition compound formed with m-nitrobenzylalcohol (NBA): $[M+H]^+$ and $[M+H+NBA]^+$. In the examples the FAB spectra data were specified accordingly. The ESI positive ionization measurements were performed in a VG Quattro (Fisons) apparatus. The samples were dissolved in a mixture of acetonitrile—water (1:1) containing 1% (v/v) of formic acid and were introduced with a 10 mL sample-loop into the ion source at a flow rate of 15–25 mL/min.

The specific rotations ($[\alpha]_D$) were determined at 20° C.

EXAMPLE 1

D-2-Cycloheptyl-2-hydroxyacetyl-L-prolyl-L-arginine aldehyde (D-cHga-Pro-Arg-H) hemisulfate Step 1: Tetrahydropyranyl-D-2-cycloheptyl-2-hydroxyacetyl-L-prolyl-$N^G$-banzyloxycarbonyl-L-arginine lactam 7.85 g (20.1 mmole) of tert-butyloxycarbonyl-$N^G$-benzyloxycarbonyl-L-arginine lactam [(S. Bajusz et al., J. Med.Chem. 33, 1729 (1990)] is suspended in 20 mL of chloroform, then 20 mL of ethyl acetate saturated with HCl gas (0.11–0.15 g/mL) is added under stirring and ice-cooling. The cleaving of the Boc group is monitored by thin-layer chromatography [$R_f(3)$=0.5 (free compound); 1.0 (Boc-compound)]. By the end of the reaction the suspension is diluted with 40 mL of diethyl ether, the crystal mass formed is filtered, washed with 10 mL of acetone and 10 mL of diethyl ether, and dried at reduced pressure over potassium hydroxide for two hours. The resulting $N^G$-benzyloxycarbonyl-L-arginine lactam hydrochloride is dissolved in 20 mL of dimethyl formamide, cooled to −20° C. and added to the following mixed anhydride.

7.1 g (20.1 mmole) of tetrahydropyranyl-D-2-cycloheptyl-2-hydroxyacetyl-L-proline (Example 1, Step 1) is dissolved in 20 mL of dimethyl formamide, cooled to −20° C., then under stirring 2.23 mL (20.1 mmole) of N-methyl-morpholine, 2.65 mL (20 1 mmole) of isobutyl chloroformate, after 10 minutes of stirring the above dimethyl formamide solution of $N^G$-benzyloxycarbonyl-L-arginine lactam and finally triethylamine are added in a quantity to adjust the pH of the reaction mixture to 8 (about 2.8 mL is required). The reaction mixture is stirred at −10° C. for 30 minutes, then at 0° C. for one hour. Thereafter the salts are filtered off and the filtrate is diluted with 100 mL of ethyl acetate. The resulting solution is washed with 3×25 mL of water, 10 mL of 1 M potassium hydrogen sulfate and 3×10 mL of water, dried over anhydrous sodium sulfate solution and evaporated at 2.0–2.5 kPa. The product obtained is submitted to silica gel column chromatography using 200 g of Kieselgel 60 as adsorbent and ethyl acetate as eluent. The fractions containing solely the pure product [$(R_f(1)$=0.60] are pooled and evaporated at 2.0–2.5 kPa. The evaporation residue is recrystallized from disopropyl ether.

Yield 8.1 g (64%), $R_f(1)$=0.6

M.p.: 66–68° C.

FAB mass spectrum (626 $[M+H]^+$, 779 $[M+H+NBA]^+$) confirms the assumed structure.

Step 2: Tetrahydropyranyl-D-2-cycloheptyl 2-hydroxyacetyl-L-prolyl-$N^G$-benzyloxycarbonyl-L-arginine aldehyde 8.0 g (12.8 mmole) of tetrahydropyranyl-D-2-cycloheptyl-2-hydroxyacetyl-L-prolyl-$N^G$-benzyloxycarbonyl-L-arginine lactam (Example 1, Step 1) is dissolved in 15 ml of tetrahydrofuran, then under stirring and at temperatures not exceeding −50° C. a solution of 3.6 mmole of lithium aluminium hydride dissolved in tetrahydrofuran is added. The progress of reduction is monitored by thin-layer chromatography using ethyl acetate—pyridine—acetic acid—water (240:20:6:11) as developing solvent and, if required, a further portion of lithium aluminium hydride is added. To this reaction mixturs 0.5 M of sulfuric acid is added dropwise under constant stirring and cooling until pH 3 is attained, then 35 mL of water is added. The resulting solution is extracted with 2×15 mL of hexane, then with 3×20 mL of methylene chloride. The methylene chloride extracts are pooled, washed with 3×15 mL of water, 15 mL of cold 5% sodium hydrogen carbonate solution and again with 15 mL of water, dried over anhydrous sodium sulfate and evaporated at 2.0–2.5 kPa. The evaporation residue is treated with diisopropyl ether, filtered and dried at reduced pressure.

Yield 7.25 g (90%), $R_f(6)=0.40$

M.p.: 107° C.

$[\alpha]_D=+16.0°$ (c=1, tetrahydrofuran)

FAB mass spectrum (628 $[M+H]^+$, 731 $[M+H+NBA])^+$) confirms the assumed structure.

Step 3: D-2-Cycloheptyl-2-hydroxyacetyl-L-prolyl-L-arginine aldehyde hemisulfate 7.05 g (11.23 mmole) of tetrahydropyranyl-D-2-cycloheptyl-2-hydroxyacetyl-L-prolyl-$N^G$-benzyloxycarbonyl-L-arginine aldehyde (Example 1, Step 2) is dissolved in 60 mL of ethanol, then 11.23 mL of 0.5 M of sulfuric acid, 13.3 mL of water and 0.7 g Pd-C catalyst, suspended in 25 mL ethanol, are added and the mixture is hydrogenated at about 10° C. The progress of the reaction is monitored by thin-layer chromatography and is completed in about 15 minutes. She catalyst is filtered and the filtrate is concentrated to about 7–9 mL at 2.0–2.5 kPa. The residue is diluted with 80 mL of water, extracted with 4×15 mL of methylene chloride and the aqueous solution is left to stand at 20–22° C. for 24 hours. The solution is again extracted with 3×15 mL of methylene chloride and the pH is adjusted to 3.5 with ion-exchange resin Dowex AG 1-X8 (HO⁻), then the solution is freeze-dried.

Yield 4.28 g (83%) $[\alpha]_D=-94.7°$ (c=1, water)

HPLC(l): k'=4.93 and 5.25

FAB mass spectrum (410 $[M+H]^+$, 563 $[M+H+NBA]^{30}$) confirms the assumed structure.

The starting material ran be prepared as follows:

Tetrahydropyranyl-D-2-cycloheptyl-2-hydroxyacetyl-L-proline (THP-D-cHga-Pro)

Step A. O-Acetyl-DL-2-cycloheptyl-2-hydroxyacetic acid dicyclohexylammonium salt 1.72 g (10 mmole) of DL-2-cycloheptyl-2-hydroxyacetic acid (H. Takeshita et al., Bull Chem. Soc. Japan 47, 1767 (1974)] is dissolved in 20 ml of anhydrous pyridine, 9.4 mL (100 mmole) of acetic anhydride is added and the solution is left to stand at room temperature for 24 hours, then it is evaporated at 2.0–2.5 kPa and the evaporation residue is dissolved in 25 mL of diethyl ether. The solution is washed with water, 1 M potassium hydrogen sulfate solution and again with water, then it is dried over anhydrous sodium sulfate and evaporated. The residue is dissolved in diethyl ether, then 2.1 mL (10.5 mmole) of dicyclohexylamine and 20 mL of cyclohexane are added. The solution is left in the refrigerator for 2 days. The crystals formed are filtered, washed with 3×10 mL of n-hexane and air-dried.

Yield 2.56 g (64.6%)

Analysis for $C_{23}H_{41}NO_4$ (395.57)

Calculated: C %=69.83; H %=10.45; N %=3.54.

Found: C %=69.9; H %=10.7; N %=3.5.

Step B. Resolution of O-acetyl-DL-2-cycloheptyl-2-hydroxyacetic acid with acylase l enzyme 1.58 g (4.0 mmole) of O-acetyl-DL-2-cycloheptyl-2-hydroxyacetic acid dicyclohexylammonium salt is dissolved in 15 mL of diethyl ether and 5 mL of 1 M potassium hydrogen sulfate solution. The phases are separated, the diethyl ether phase is washed to neutrality, dried over anhydrous sodium sulfate and evaporated. The residue, 0.86 g (4.0 mmole) of an oil—O-acetyl-DL-2-cycloheptyl-2-hydroxyacetic acid—is dissolved in 20 mL of 0.2 M of sodium hydrogen carbonate, then 0.01 gof cobalt(II)chloride hexahydrate and 0.005 mg of acylase l enzyme (Sigma, 2000–3000 units/mg) are added and the solution is left to stand at about 25° C. for 3 days. The aqueous solution is acidified with 4.5 mL of 1 M potassium hydrogen sulfate solution and extracted with 3×10 mL of diethyl ether. The diethyl ether phases are pooled, washed with water, dried over anhydrous sodium sulfate and evaporated. The evaporation residue is an oil, a mixture of L-2-cyclo-heptyl-2-hydroxyacetic acid [$R_f(14)=0.2$], formed upon the action of the enzyme, and O-acetyl-D-2-cycloheptyl-hydroxyacetic acid [$R_f(14)=0.5$] which is not cleaved by the enzyme. The mixture is submitted to chromatography on a silica gel column, using a mixture of chloroform—acetic acid (95:5) as developing solvent. The fractions containing solely the pure product are pooled and evaporated at 2.0–2.5 kPa.

Evaporation residue 1 is O-acetyl-D-cycloheptyl-2-hydroxyacetic acid [$R_f(14)=0.2$], 0.34 g (79%) of an oil which is used directly in the next step C.

Evaporation residue 2 is L-2-cycloheptyl-2-hydroxyacetic acid [$R_f(14)=0.2$], 0.25 g (80%) of a solid compound, which is filtered with n-hexane and air-dried.

M.p.: 78° C.

$[\alpha]_D=+18.15°$ (c=1, methanol). Optical purity about 95% (chiral HPLC).

Step C: D-2-Cycloheptyl-2-hydroxyacetic acid (deacetylation of O-acetyl derivative with sodium methylate)

O-Acetyl-D-2-cycloheptyl-2-hydroxyacetic acid (evaporation residue 1), obtained in Step B, is dissolved in 4 ml of methanol containing 1.59 mmole of sodium methylate. The solution is left to stand for 24 hours, then it is evaporated. The residue is dissolved in 10 mL of diethyl ether and 2.5 mL of 0.5 M potassium hydrogen sulfate solution, the diethyl ether phase is washed with water, dried over anhydrous sodium sulfate and evaporated. The crystalline residue is worked up with hexane, filtered and air-dried.

Yield 0.21 g (61%)

$[\alpha]_D=-14.7°$ (c=1, methanol). Optical purity about 86% (chiral HPLC).

Step D: D-2-Cycloheptyl-2-hydroxyacetic acid (resolution of DL-compound with D-tyrosine)

17.2 g (100 mmole) of DL-2-cycloheptyl-2-hydroxyacetic acid and 19.52 g (100 mmole) of D-tyrosine hydrazide are suspended in 600 mL of anhydrous ethanol and refluxed up to full dissolution. The solution is left to cool first to room temperature, then it is left in the refrigerator overnight. The crystals formed are filtered, washed with 2×20 mL of anhydrous ethanol and dried under reduced pressure. The product, 19.54 g (53.18 mmole) of diastereomer salt, is recrystallized twice from 15 mL/g of anhydrous ethanol. 12.45 g (67.7%) of the diastereomer salt is obtained which is dissolved in 50 mL of diethyl ether and 50 mL of 1 M potassium hydrogen sulfate. The diethyl ether phase is washed with water to neutrality, dried over anhydrous sodium sulfate and evaporated at 2.0–2.5 kPa. The crystalline residue is worked up with n-hexane, filtered and air-dried.

Yield 5.61 g (32.57 mmole, 65.2%) of D-2-cycloheptyl-2-hydroxyacetic acid.

M.p.: 80° C.

$[\alpha]_D$=−20.2° (c=1, methanol) and −30° (c=1, acetic acid).

Optical purity>98% (chiral HPLC).

Analysis for $C_9H_{18}O_3$ (172.22)

Calculated: C %=62.76; H %=9.36;

Found: C %=62.01; H %=9.31.

Step E: D-2-Cycloheptyl-2-hydroxyacetic acid benzyl ester 5.51 g (32 mmole) of D-2-cycloheptyl-2-hydroxyacetic acid (Example 1, Step D) is dissolved in 37 mL of dimethyl formamide, then 3.7 mL (31.3 mmole) of benzyl bromide and 6.34 mL (32 mmole) of dicyclohexyl carbodiimide are added and the mixture is stirred for 24 hours at room temperature. Thereafter the reaction mixture is filtered and evaporated at 2.0–2.5 kPa. The residue is dissolved in 50 mL of diethyl ether and 50 mL of 0.5 M potassium hydrogen sulfate. The diethyl ether phase is washed with water to neutrality, 2×10 mL of 5% sodium hydrogen carbonate and 2×10 mL of water, dried over anhydrous sodium sulfate and evaporated at 2.0–2.5 kPa.

Yield 7.4 g (88%) oil, $R_f(12)$=0.20

$[\alpha]_D$=+13.2° (c=1, methanol).

Step F: Tetrahydropyranyl-D-2-cycloheptyl-2-hydroxyacetic acid benzyl ester 7.4 g (28 mmole) of D-2-cycloheptyl-2-hydroxyacetic acid benzyl ester (Example 1, Step E) is dissolved in 65 mL of methylene chloride, then 3.6 mL (39.4 mmole) of 2,4-dihydropyrane and 0 3 mL of ethyl acetate saturated with HCl gas (0.11–0.15 g/mL) are added and the solution is left to stand at room temperature for 16 hours. Thereafter the reaction mixture is diluted with 40 mL of methylene chloride, washed with 3×20 mL of water, 3×20 mL of cold 5% sodium hydrogen carbonate solution, again with 2×20 mL of water, dried over anhydrous sodium sulfate and evaporated at 2.0–2 5 kPa. The residue is considered 28 mmole of tetrahydro-pyranyl-D-2-cycloheptyl-2-hydroxyacetic acid benzyl ester [$R_f(12)$=0.30].

Step G: Tetrahydropyranyl-D-2-cycloheptyl-2-hydroxyacetic acid 28 mmole of tetrahydropyranyl-D-2-cycloheptyl-2-hydroxyacetic acid benzyl ester (Example 1, Step F) is dissolved in 50 mL of methanol and hydrogenated in the presence of 0.1 g of Pd-C catalyst. The progress of the reaction is monitored by thin-layer chromatography [$R_f$(12)=0.30 (ester), 0.00 (acid); $R_f(2)$=1.00 (ester); 0.8 (acid)]. By the end of the reaction the catalyst is filtered, the filtrate is evaporated at 2.0–2.5 kPa and the oil residue is dried under reduced pressure.

Yield 6.7 g (25 mmole, 89%) oil, [$R_f(2)$=0.80].

Step H: Tetrahydropyranyl-D-2-cycloheptyl-2-hydroxyacetyl-L-proline benzyl ester 25 mmole of tetrahydropyranyl-D-2-cycloheptyl-2-hydroxyacetic acid (Example 1, Step G) is dissolved in 25 mL of dimethyl formamide, then 2.8 mL (25 mmole) of N-methylmorpholine, 6.04 g (25 mmole) of L-proline benzyl ester hydrochloride, thereafter under stirring and ice-cooling 5.16 g (25 mmole) of dicyclohexyl carbodimide are added. The reaction mixture is stirred for one hour at 0° C. and overnight at room temperature, finally it is filtered and evaporated at 2.0–2.5 kPa. The residue is dissolved in 100 mL of diethyl ether, washed with 3×20 mL of 5% sodium hydrogen carbonate solution, water, 1 M potassium hydrogen sulfate solution and water, dried over anhydrous sodium sulfate and evaporated. The evaporation residue is dried under reduced pressure Yield 9.9 g (90%) oil, $R_f(1)$=0.80.

Step I: Tetrahydropyranyl-D-2-cycloheptyl-2-hydroxyacetyl-L-proline 9.9 g (22.5 mmole) of tetrahydropyranyl-D-2-cycloheptyl-2-hydroxyacetyl-L-proline benzyl ester (Example 1, Step H) is dissolved in 100 mL of methanol and hydrogenated in the presence of 0.1 g of Pd-C catalyst. The progress of the reaction is monitored by thin-layer chromatography [$R_f(1)$=0.80 (ester), 0.00 (acid); $R_f(2)$=1.00 (ester); 0.30 (acid)]. By the end of the reaction the catalyst is filtered, the filtrate is evaporated at 2.0–2.5 kPa and the oil residue is dried under reduced pressure. Yield 7.2 g (90%) oil, $R_f(2)$=0.30, a major portion of which is directly used in Example 1, Step 1, and a small portion is converted to a crystalline salt as follows.

0.35 g (1 mmole) of tetrahydropyranyl-D-2-cycloheptyl-2-hydroxyacetyl-L-proline (oil) is dissolved in 5 mL of diethyl ether and 0.115 mL (1.05 mmole) of cyclohexylamine is added. The crystals formed are filtered, washed with diethyl ether and dried at reduced pressure.

Yield 0.40 g (90%) of tetrahydropyranyl-D-2-cycloheptyl-2-hydroxyacetyl-L-proline cyclohexylammonium salt.

M.p.: 146–150° C.

$[\alpha]_D$=−12.8° (c=1, ethanol).

Analysis for $C_{25}H_{44}N_2O_5$ (452.62)

Calculated: C %=66.34; H %=9.80; N %=6.19;

Found: C %=66.20; H %=9.90; N %=6.08.

EXAMPLE 2

D-2-Cyclopentyl-2-hydroxyacetyl-L-prolyl-L-arginine aldehyde (D-cPga-Pro-Arg-H) hemisulfate Step 1: Tetrahydropyranyl-D-2-cyclopentyl-2-hydroxyacetyl-L-prolyl-$N^G$-benzyloxycarbonyl-L-arginine lactam 0.82 g (2.1 mmole) of tert-butyloxy-carbonyl-$N^G$-benzyloxycarbonyl-L-arginine lactam [S. Bajusz et al., J. Med. Chem. 33, 1729 (1990)] and tetrahydropyranyl-D-cyclopentyl-2-hydroxyacetyl-L-proline (Example 2, Step G) are coupled. Using the process described in Example 1, Step 1, and utilizing proportional amounts of reagents and solvents, the final product is purified by chromatography. The fractions containing solely the pure final product [$R_f$(1)=0,4] are pooled, evaporated at 2.0–2.5 kPa and the residue is dried at reduced pressure. Yield 0.59 g (47%) oil which is considered 0.97 mmole of tetrahydropyranyl-D-2-cyclopentyl-2-hydroxyacetyl-L-prolyl-$N^G$-benzyloxycarbonyl-L-arginine lactam. The FAB mass spectrum confirms the assumed structure: (598 [M+H]$^+$, 751 [M+H+NBA]$^+$.

Step 2: Tetrahydropyranyl-D-2-cyclopentyl-2-hydroxyacetyl-L-prolyl-$N^G$-benzyloxycarbonyl-L-arginine aldehyde 0.56 g (0.98 mmole) of tetrahydropyranyl-D-2-cyclopentyl-2-hydroxyacetyl-L prolyl-$N^G$-benzyloxycarbonyl-L-arginine lactam (Example 2, Step 1) is reduced by the process described in Example 1, Step 2, using proportional amounts of reagents and solvents, except that the thin-layer chromatography monitoring the progress of the reaction is run in ethyl acetate [$R_f(1)$=0.4 (lactam), 0.0 (aldehyde)].

Yield 0.4 g (67%) of the aimed product after working up with hexane. $R_f(6)$=0.4 (lactam).

M.p.: 91–93° C.

The FAB mass spectrum confirms the assumed structure: (600[M+H]$^+$, 753[M+H+NBA]$^+$).

Step 3: D-2-Cyclopentyl-2-hydroxyacetyl-L-prolyl-L-arginine aldehyde hemisulfate 0.38 g (0 63 mmole) of tetrahydropyranyl-D-2-cyclopentyl-2-hydroxyacetyl-L-prolyl-$N^G$-benzyloxycarbonyl-L-arginine aldehyde (Example 2, Step 2) is transformed, by the process described in Example 1, Step 3, using proportional amounts of reagents and solvents.

Yield 0.22 g (81%) of the aimed product, HPLC(l): k'=4.29 and 4.68.

The FAB mass spectrum confirms the assumed structure: $(382[M+H]^+, 535[M+H+NBA]^+)$.

The starting materials can be prepared as follows:

Tetrahydropyranyl-D-2-cyclopentyl-2-hydroxyacetyl-L-proline (THP-D-cPga-Pro)

Step A: Resolution of O-acetyl-DL-2-cyclopentyl-2-hydroxyacetic acid with acylase enzyme 0.72 g (5.0 mmole) of DL-2-cyclopentyl-2-hydroxyacetic acid [M. Robba and Y. Le Guen, Chim. Therap. 1966, 238; Chem. Abst. 66, 18633f (1967)] is acetylated and hydrolyzed with acylase l by the process described in Example 1, Steps A and B, using proportional amounts of reagents and solvents. The resulting mixture of L-2-cyclopentyl-2-hydroxyacetic acid $[R_f(14)=0.35]$ and O-acetyi-D-2-cyclopentyl-2-hydroxyacetic acid $[R_f(14)=0.52]$ is separated and the latter one is transformed by the process described in Example 1, Step C, using proportional amounts of reagents and solvents, into D-2-cyclopentyl-2-hydroxyacetic acid. Yield:

a) 0.2 g (1.39 mmole) of L-2-cyclopentyl-2-hydroxyacetic acid, m.p. 108–109° C.;
$[\alpha]_D=-15.95°$ (c=1, methanol); optical purity 99% (chiral HPLC), and b) 0.16 g (1.1 mmole) of D-2-cyclopentyl-2-hydroxyacetic acid, m.p. 106° C.; $[a\alpha]_D=+15.5°$ (c=1, methanol); optical purity 98% (chiral HPLC).

Step B: D-2-Cyclopentyl-2-hydroxyacetic acid (resolution of DL-compound with D-tyrosine hydrazide)

1.44 g (10 mmole) of DL-2-cyclopentyl-2-hydroxyacetic acid [M. Robba and Y. Le Guen, Chim. Therap 1966, 238; Chem Abst 66, 18633f (1967)] and 1.97 g (10 mmole) of D-tyrosine hydrazide are suspended in 50 mL of anhydrous ethanol and refluxed up to full dissolution. Then the solution is left to cool to room temperature and kept in the refrigerator overnight. The crystals formed are filtered, washed with 2×2 mL of cold, anhydrous ethanol and dried at reduced pressure. The obtained 2.14 g (6.3 mmole) of diastereomer salt is recrystallyzed twice from 40 mL of anhydrous ethanol. The resulting 1.54 g (4.53 mmole) of diastereomer salt is dissolved in 10 mL of diethyl ether and 5 mL of 1 M potassium hydrogen sulfate solution. The diethyl ether phase is washed to neutrality with water, dried over anhydrous sodium sulfate and evaporated at 2.0–2.5 kPa. The crystalline residue is worked up with petroleum ether, filtered and air-dried.

Yield 0.56 g (3.88 mmole. 76.7%) of D-cyclopentyl-2-hydroxyacetic acid, m.p. 109–110° C.;
$[\alpha]_D=+14.8°$ (c=1, methanol) and −30° (c=1, acetic acid). Optical purity 98% (chiral HPLC).
Analysis for $C_7H_{12}O_3$ (144.17)
Calculated: C %=58.31; H %=8.39;
Found: C %=58.56; H %=8.50.

Step C: D-2-Cyclopentyl-2-hydroxyacetic acid benzyl ester 0.47 g (3.2 mmole) of D-2 cyclopentyl-2-hydroxyacetic acid (Example 2, Step B) is transformed by the process described in Example 1, Step E, using proportional amounts of reagents and solvents.

Yield 0.74 g (95%) of the aimed product in oil form $[R_f(12)=0.20]$.

Step D: Tetrahydropyranyl-D-2-cyclopentyl-2-hydroxyacetic acid benzyl ester 0.74 g (3.2 mmole) of D-2-cyclopentyl-2-hydroxyacetic acid benzyl ester (Example 2, Step C) is transformed by the process described in Example 1, Step F, using proportional amounts of reagents and solvents. The resulting evaporation residue is considered 2.75 mmole of the aimed product $R_f(12)=0.27–0.36$.

Step E: Tetrahydropyranyl-D-2-cyclopentyl-2-hydroxyacetic acid 2.75 mmole of tetrahydropyranyl-D-2-cyclopentyl-2-hydroxyacetic acid benzyl ester (Example 2, Step D) is transformed by the process described in Example 1, Step G, using proportional amounts of reagents and solvents.

Yield 0.6 g (2.6 mmole, 95%) of the aimed product $[R_f(1)=0.25]$.

Step F: Tetrahydropyranyl-D-2-cyclopentyl-2-hydroxyacetyl-L-proline benzyl ester 2.6 mmole of tetrahydropyranyl D-2-cyclopentyl-2-hydroxyacetic acid (Example 2, Step E) and 0.62 g (2.6 mmole) of 1-proline benzyl eater hydrochloride are condensed by the process described in Example 1. Step H, using proportional amounts of reagents and solvents.

Yield 0.97 g (90%) of the aimed product in oil form. $R_f(1)=0.7$.

Step G: Tetrahydropyranyl-D-2-cyclopentyl-2-hydroxyacetyl-L-proline 0.97 g (2.3 mmole) of tetrahydropyranyl-D-2-cyclopentyl-2-hydroxyacetyl-L-proline benzyl ester (Example 1, Step F) is transformed by the process described in Example 1, Step I, using proportional amounts of reagents and solvents.

Yield 0.71 g (89%) of the aimed product in oil form $[R_f(9)=0.5]$, a major portion of which is used directly in Step 1 of the Example and a small portion is converted to a crystalline salt as follows.

0.03 g (0.1 mmole) of tetrahydropyranyl-D-2-cyclopentyl-2-hydroxyacetyl-L-proline (oil) is dissolved in 5 mL of diethyl ether and 0.018 mL (0.1 mmole) of dicyclohexylamine is added. The crystals formed are filtered, washed with diethyl ether and dried at reduced pressure.

Yield 0.048 g (95%) of tetrahydropyranyl-D-2-cyclopentyl-2 hydroxyacetyl-L -praline dicyclohexylammonium salt M.p.: 145–147° C.
Analysis for $C_{29}H_{50}N_2O_5$ (506.73)
Calculated: C %=68.13; H %=9.95; N %=5.52;
Found: C %=67.25; H %=9.94; N % =6.20.

The FAB mass spectrum confirms the assumed structure: $(507[M+H+DCHA]^+)$.

Methods

Method M1

Preparation of Plasma Clot a) Platelet-rich plasma (PRP) is prepared by centrifuging a 9:1 mixture of human blood and 3.8% aqueous sodium citrate solution (1/2) for 5 minutes at 240×g.

b) 200 μL of PRP are placed in each reaction vessel, 80 μL of 40 mM calcium chloride solution is added and the mixture is left to stand at room temperature for one hour. The plasma clot formed is rinsed mildly with 6×2 ml of 0.9% sodium chloride solution followed by 5 minute sedimentation to remove the dissolved enzymes (factor Xa and thrombin). The thrombin content of the washings is assayed as follows.

c) To 400 μL of washing liquid 100 μL of 1 mM Tos-Gly-Pro-Arg-pNA substrate solution is added and the mixture is incubated for 30 minutes at 37° C., then the reaction is stopped by the addition of 100 μL of 50% acetic acid. 150 μL portions of this mixture are transferred into the wells of the 96-well microtiter plate and the extinction is measured at 405 nm (ELISA READER SLT Laborinstrument GmbH, Austria). When the washing is successful, the extinction is less than 5% of the control Method M2

Assay of the Inhibition of Factor Xa Entrapped in Plasma Clot a) 0.1–1.0–10 and 100 μg/mL solutions of the peptide inhibitor are prepared with 0.1 M Tris buffer containing 0.02% human albumin at pH 8.5.

b) After draining the washing liquid, 400 μL of the peptide solution (3 parallel samples for each concentration) and 400 μL of buffer, serving as control, are placed on the clot (Method M1) and the mixture is incubated for 5 minutes at 37° C. Thereafter 100 μL of 2 mM Moc-D-Chg-Gly-Arg-pNA substrate solution is added and incubation at 37° C. is continued for further 30 minutes, then the reaction is stopped by the addition of 100 μL of 50% acetic acid.

c) 150 μL portions of each reaction mixture are placed into the wells of a 96-well microtiter plate and the extinction is determined at 405 nm (ELISA READER SLT Laborinstrument GmbH, Austria). The peptide concentration ($IC_{50}$) required for 50% inhibition is determined graphically from the mean extinction values related to the controls.

Method M3

Assay of the Inhibition of Thrombin Entrapped in Plasma Clot a) Peptide inhibitor solutions are prepared by the process described in Method M2, point a).

b) After draining the washing liquid, 400 μL of the peptide solution (3 parallel samples for each concentration) and 400 μL of buffer, serving as control, are placed on the clot (Method M1) and the mixture is incubated for 5 minutes at 37° C. Thereafter 100 μL of mM Tos-Gly-Pro-Arg-pNA substrate solution is added and incubation at 37° C. is continued for further 30 minutes, then the reaction is stopped by the addition of 100 μL of 50% acetic acid. The operation is continued as described in Method M2, point c).

Method M4

Preparation of Fibrin-Gel a) 200 μL of 6 mg/mL human fibrinogen (SIGMA), 25 μL of 25 NIH U/mL human thrombin (SIGMA) and 40 μL of 100 mM calcium chloride solution are placed in each reaction vessel and the mixtures are stored for one hour at 20–22° C. The fibrin formed is rinsed mildly with 3×2 ml of isotonic saline solution followed by sedimentation to remove the thrombin content of the solution. The efficacy of rinsing is controlled by the process described in Method M1, point c).

Method M5

Assay of the Inhibition of Thrombin Bound to Fibrin-Gel a) 0.1–1.0–10 and 100 μg/ml solutions are prepared with Hepes/NaCl buffer (0.01 M Hepes and 0.1 M sodium chloride, pH=7.4).

b) Thereafter the procedure described in Method M3, point b) is followed.

Method M6

Assay of the Inhibition of Factor Xa in Solution on a 96-well Microtiter Plate a) 1.3 U/mL factor Xa (human, SIGMA), 0.1–1.0–10 and 100 μg/mL solutions in phosphate buffer (0.1 M sodium phosphate and 0.05 M sodium chloride, pH 7.4) of the peptide inhibitors and 0.33 nM solutions of the substrate Bz-Ile-Glu-Gly-Arg-pNA in distilled water are used.

b) Three reaction mixtures are prepared from the control and each peptide solution. 30 μL each of the peptide and the buffer, serving as control, 30 μL factor Xa, 90 μL butter and 150 μL substrate are placed in the wells of the plate, then after 10 minutes the extinction values are read at 405 nm The procedure is continued as described in Method M2, point c).

What we claim is:

1. A compound of formula (I),

D-Xaa-Pro-Arg-H                    (I)

wherein

Xaa represents a 2-cycloheptyl-2-hydroxyacetyl or 2-cyclopentyl-2-hydroxyacetyl group, Pro represents an L-prolyl residue and Arg represents an L-arginyl residue, or an acid-addition salt thereof formed with an organic or inorganic acid.

2. D-2-Cycloheptyl-2-hydroxyacetyl-L-prolyl-L-arginine aldehyde and its acid-addition salts.

3. D-2-Cycloheptyl-2-hydroxyacetyl-L-prolyl-L-arginine aldehyde hemisulfate.

4. D-2-Cyclopentyl-2-hydroxyacetyl-L-prolyl-L-arginine aldehyde and its acid-addition salts.

5. D-2-cyclopentyl-2-hydroxyacetyl-L-prolyl-L-arginine aldehyde hemisulfate.

6. A pharmaceutical composition which comprises as active ingredient at least one compound of formula (I), wherein Xaa, Pro and Arg are as defined in claim 1, or a pharmaceutically acceptable acid-addition salt thereof in admixture with pharmaceutically acceptable solvents, diluents, carriers and/or additives.

7. A method of treating thrombosis and/or hypercoagulability-associated diseases, which method comprises administering to a mammal in need there of an effective amount of the formula (I) compound as defined in claim 1.

8. The method of claim 7, wherein the disease associated with thrombosis and/or hypercoagulability is selected from the group consisting of deep vein thrombosis, pulmonary embolism, arterial thrombosis, unstable angina, myocardial infarct, auricular fibrillation, stroke, coronary artery disease and thrombolic diseases of coronary arteries.

9. A method of preventing the reocclusion of arteries, which method comprises administering to a mammal in need there of an effective amount of compound of formula (I), as defined in claim 1.

* * * * *